United States Patent
Sefton et al.

(10) Patent No.: US 11,439,172 B2
(45) Date of Patent: Sep. 13, 2022

(54) MICROBIAL BIOMASS BASED FEED PRODUCTS

(71) Applicant: OAKBIO, INC., Sunnyvale, CA (US)

(72) Inventors: Brian A Sefton, Cupertino, CA (US); William J Coleman, Redwood City, CA (US)

(73) Assignee: OAKBIO, INC., Sunnyvale, CA (US)

(*) Notice: Subject to any disclaimer, the term of this patent is extended or adjusted under 35 U.S.C. 154(b) by 529 days.

(21) Appl. No.: 15/641,114

(22) Filed: Jul. 3, 2017

(65) Prior Publication Data

US 2019/0000124 A1 Jan. 3, 2019

(51) Int. Cl.

| | |
|---|---|
| *A23L 33/135* | (2016.01) |
| *C12N 1/20* | (2006.01) |
| *C12M 1/00* | (2006.01) |
| *A23K 20/10* | (2016.01) |
| *A23K 50/80* | (2016.01) |
| *A23K 10/16* | (2016.01) |
| *A23J 1/00* | (2006.01) |

(52) U.S. Cl.
CPC .............. *A23L 33/135* (2016.08); *A23J 1/008* (2013.01); *A23K 10/16* (2016.05); *A23K 20/10* (2016.05); *A23K 50/80* (2016.05); *C12M 29/20* (2013.01); *C12N 1/20* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 5,266,096 | A * | 11/1993 | Slavensky | C05F 11/08 435/252.4 |
| 6,855,526 | B2 * | 2/2005 | Saha | C12P 7/18 435/105 |
| 7,579,163 | B2 * | 8/2009 | Eriksen | A23J 1/005 435/252.1 |
| 9,206,451 | B2 * | 12/2015 | Sefton | C12P 7/62 |
| 2013/0189763 | A1 * | 7/2013 | Dalla-Betta | C12M 29/02 435/252.1 |

FOREIGN PATENT DOCUMENTS

| | | |
|---|---|---|
| CN | 100494122 C | 6/2009 |
| CN | 103496791 A | 1/2014 |
| CN | 104512968 A | 4/2015 |
| CN | 108220205 A | 6/2018 |
| KR | 20130000366 A | 1/2013 |
| WO | 2017165244 A1 | 9/2017 |

OTHER PUBLICATIONS

Zhu et al. Proc. Natl. Acd. Sci. USA, 1988, vol. 85, pp. 4209-4213.*
PCT/US18/40557 International Search Report and Written Opinion dated Sep. 19, 2018.
EP 18828251, EESR Dated Nov. 16, 2020.

* cited by examiner

*Primary Examiner* — Vera Afremova
(74) *Attorney, Agent, or Firm* — Rimon Law, P.C.

(57) ABSTRACT

Aquafeed, animal feed, and other food products, as well as nutritional and pharmaceutical compounds, chemicals and biomaterials are important commodities that can be produced at commercial scale by fermentation of microorganisms. The present invention provides a method for producing these valuable multi-carbon compounds from simple gas feedstocks, such as carbon dioxide, hydrogen and oxygen, by cultivating a consortium of microbial cells specially selected for this purpose in an aqueous culture medium. In addition to exploiting inexpensive feedstocks, such as waste industrial gas for this cultivation, the platform described herein also provides the advantage of removing carbon dioxide and other waste gases from industrial emissions, which would otherwise contribute to global climate change. Furthermore, the cultivation of a microbial consortium can provide highly nutritious components to a feed blend that might not be available from a monoculture.

1 Claim, 2 Drawing Sheets

MICROBIAL BIOMASS BASED FEED PRODUCTS

CROSS-REFERENCE TO RELATED APPLICATION

This application is a continuation in part of U.S. patent application Ser. No. 13/968,723 filed on Aug. 16, 2013;
Ser. No. 13/968,723 is a continuation in part of U.S. patent application Ser. No. 13/610,844 filed Sep. 11, 2012 now U.S. Pat. No. 9,206,451 issued Dec. 8, 2015; Ser. No. 13/610,844,
Ser. No. 13/610,844 claimed priority to U.S. provisional application 61/640,459 filed Apr. 30, 2012 and 61/533,672 filed Sep. 12, 2011;
Ser. No. 13/968,723 is further a continuation in part of U.S. patent application Ser. No. 12/726,980 filed Mar. 18, 2010 now U.S. Pat. No. 8,518,566, Ser. No. 12/726,980 claimed benefit of provisional application 61/161,331 filed Mar. 18, 2009;
Ser. No. 13/968,723 is further a continuation in part of U.S. patent application Ser. No. 13/034,596 filed Feb. 24, 2011, Ser. No. 13/034,596 claimed benefit of 61/308,050 filed Feb. 25, 2010 and 61/371,623 filed Aug. 6, 2010;
Ser. No. 13/968,723 is further a continuation in part of U.S. patent application Ser. No. 13/204,649 filed Aug. 6, 2011, Ser. No. 13/204,649 claimed benefit of 61/371,623 filed Aug. 6, 2010;
Ser. No. 13/968,723 is further a continuation in part of U.S. patent application Ser. No. 13/841,704 filed Mar. 15, 2013, Ser. No. 13/841,704 claimed benefit of 61/640,459 filed Apr. 30, 2012;
this application is a continuation in part of U.S. patent application Ser. No. 14/601,976 filed Jan. 21, 2015, Ser. No. 14/601,976 claimed benefit of 61/929,853 filed Jan. 21, 2014;
this application further claims the benefit of U.S. Provisional Patent Application Ser. No. 62/358,048 filed on Jul. 3, 2016 and entitled "Novel Microbial Biomass Based Feed Products."
All of the above patent applications are hereby incorporated herein by reference.

BACKGROUND

Field of the Invention

The present invention is generally related to the fields of microbial fermentation and industrial biotechnology, including biological methods, processes and microorganisms for producing, via gas fermentation, nutritional products including high-protein food, food additives and other products from the gas streams which contain carbon and energy, which may be by-products, side products or products of various industrial processes.

Related Art

Gas feedstocks represent a vast resource of carbon and energy that can be used to grow chemoautotrophic microorganisms for use in human and animal nutritional products. Chemoautotrophic bacteria are capable of capturing and metabolizing carbon from inorganic sources, such as $CO_2$, CO, $CH_4$, as well as, in some cases, hydrogen ($H_2$) or methane ($CH_4$) as a primary or additional source of energy. By converting inorganic carbon to organic carbon via metabolic carbon fixation, these microbes can serve as primary producers in natural environments. Many of these chemoautotrophic species can be cultured on gas feedstocks in bioreactors for commercial production of biomass, which can be processed into nutritional products such as animal feed, companion animal feed, or even food for humans, and chemicals.

A microbial consortium is defined as two or more microbial species living symbiotically. Microbial co-cultures. For the consortia described as part of the present invention, chemoautotrophic microbes are employed in a system where the primary source of carbon and energy are both supplied as gases, such that the primary producers support a defined consortium of bacterial species via mutualistic interactions. The consortium of various defined species in the present invention, when harvested, can be used as a nutritional product. In order to make more ideal nutritional products, it is desirable to grow multiple different species together, each of which provides different nutritional properties. The use of multiple microbes allows controlled modification and customization of the nutritional composition of the final product. It is also possible to include one or more genetically modified strains which produce a key component, such as astaxanthin, a carotenoid which is a key ingredient for aquaculture.

A formulation of bacteria that could increase the amounts of desirable fatty acids and amino acids in the final biomass product would therefore be highly desirable.

An advantage of the present invention is that the dried biomass can be blended into an aquafeed or other nutritional product to replace the fishmeal that is normally harvested and used for feeding farmed fish and seafood, such as salmon, trout, tilapia, and shrimp. This will make a major impact on reducing the stress on the world's fisheries (Pitcher & Cheung, 2013), which will not be able to keep up with the projected demand for fishmeal.

Another advantage of the present invention is that the composition of the consortium can be adjusted to fine-tune the nutritional composition of the biomass product. This ability to make adjustments is advantageous because, for example, recent studies have shown that adapting the amino acid composition of feed given to laboratory mice based on the animal's own overall amino acid composition not only reduces the amount of feed needed, but also improves the health of the. Also, aquaculture and other animal feeds and feed additives are altered by selecting the amounts of various ingredients added to achieve desired amino acid profiles. By adjusting the consortia, a number of application specific nutritional products can be derived including for use by humans. Special consortia may even be created for aid in treating medical conditions, dietary deficiencies or to match growth stages of proposed consuming organism.

Nevertheless, bacteria comprising the genera *Bacillus, Lactobacillus, Bifidobacterium* and others, which are known to be of nutritional, and/or medicinal and/or probiotic benefit are not capable of growing on gas substrates, such as $CO_2$, $H_2$, CO and $CH_4$.

However, certain strains of chemoautotrophic microbes from the genera *Cupriavidus, Rhodobacter, Methylobacterium, Methylococcus, Rhodospirillum* and *Rhodopseudomonas*, are known to grow on gaseous substrates, such as $CO_2$, $H_2$, CO and $CH_4$.

Photoautotrophic microbes are bacteria, cyanobacteria and algae that can fix carbon from $CO_2$ by utilizing light energy. However, certain species of photoautotrophic bacteria also exhibit chemoautotrophic metabolism, in that they are able to utilize hydrogen as an energy source to drive the fixation of $CO_2$ without light. Examples of these are the genera *Rhodobacter*, *Rhodospirillum* and *Rhodopseudomonas*. Many other such species are known in the literature. *C. necator* has been shown to grow faster and more efficiently on CO2/H2 than typical acetogens that are used in some anaerobic gas fermentation.

Bacteria grown under chemoautotrophic conditions express different amounts (and in some cases, different types) of proteins, enzymes, transporters, fats, oils, vitamins, co-factors and other biochemicals, than do those grown in traditional fermentation. Examples of this would be cytochromes, quinones (e.g., coenzyme Q), RuBisCO (Ribulose-1,5-bisphosphate carboxylase oxygenase), as well as having overall different levels and ratios of amino acids. Because of this, bacteria grown chemoautotrophically have different nutritional profiles than the same bacteria grown heterotrophically. These growth differences can be advantages for providing additional vitamins, minerals, cofactors, etc. to the biomass product.

Bacteria grown chemoautrophically also have different secretory activity, which affects the content of the fermentation mix. Chemoautotrophic bacteria (and photoautotrophic bacteria grown chemoautotrophically) release chemicals into the growth medium, such as glycolates, polysaccharides, proteins, amino acids, fats, oils, hydrocarbons, nucleic acids, organic acids, polyhydroxyalkanoates, phasins, carotenoids, vitamins, gene transfer agents (GTA) and other biomolecules that can then be utilized by non-autotrophic bacteria and other heterotrophic microorganisms as growth substrates and growth regulators.

In an alternative embodiment, one or more of the strains in the consortium may naturally, or be genetically modified in order to, produce a valuable small molecule (e.g., a specific fatty acid) or a protein product (e.g., an enzyme, therapeutic protein, antibiotic, hormone, vitamin, precursor, antibody or vaccine). The present invention provides a means to produce such molecules using cheap gas feedstocks even if the host organism(s) cannot grow solely on gas.

In this application we describe an invention wherein a food or feed product with characteristics that provide nutritional, medical, and/or dietary benefits, and that comprises a consortium of chemoautotrophic microbes, photoautotrophic and non-chemoautotrophic microbes, is produced by cultivating these microbes on gaseous substrates. The consortium creates an ecosystem in which the chemoautotrophic microbes form the base of a food chain on which the non-autotrophic microbes are capable of growing. The goal of the gas-based fermentation process described herein is to generate a biomass product that has enhanced nutritional value compared to the biomass that the same chemoautotrophic microbes would produce if grown alone. A further economic benefit of this invention is to facilitate the growth of desired or beneficial microbes that otherwise could not utilize the inexpensive $CO_2$ or other C1 feedstocks as a primary carbon source, and/or the hydrogen (or other inorganic or C1 compounds) for energy.

A number of species of microbe are known to nutritionally beneficial, or to produce beneficial substances, or have probiotic properties which can be significant components of a product which can be produced by this method. Examples of these are: *Aspergillus niger*, *Aspergillus oryzae*, *Bacillus coagulans*, *Bacillus lentus*, *Bacillus licheniformis*, *Bacillus megaterium*, *Bacillus pumilus*, *Bacillus subtilis*, *Bacteroides amylophilus*, *Bacteroides capillosus*, *Bacteroides ruminocola*, *Bacteroides suis*, *Bifidobacterium adolescentis*, *Bifidobacterium animalis*, *Bifidobacterium bifidum*, *Bifidobacterium infantis*, *Bifidobacterium lactis*, *Bifidobacterium longum*, *Bifidobacterium thermophilum*, *Bifidobacterium breve*, *Lactobacillus acidophilus*, *Lactobacillus brevis*, *Lactobacillus bulgaricus*, *Lactobacillus casei*, *Lactobacillus cellobiosus*, *Lactobacillus curvatus*, *Lactobacillus delbruekii*, *Lactobacillus fermentum*, *Lactobacillus helveticus*, *Lactobacillus johnsonii*, *Lactobacillus lactis*, *Lactobacillus paracasei*, *Lactobacillus parafarraginis*, *Lactobacillus plantarum*, *Lactobacillus reuterii*, *Lactobacillus rhamnosus*, *Lactobacillus salivarius*, *Lactobacillus sporogenes*, *Lactococcus lactis*, *Leuconostoc mesenteroides*, *Pediococcus acidilactici*, *Pediococcus cerevisiae*, *Pediococcus pentosaceus*, *Propionibacterium shermanii*, *Propionibacterium freudenreichii*, *Saccharomyces boulardii*, *Saccharomyces cerevisiae*, *Streptococcus cremoris*, *Streptococcus diacetylactis*, *Streptococcus faecium*, *Streptococcus intermedius*, *Streptococcus lactis*, *Streptococcus thermophiles*.

SUMMARY

Figure 1:
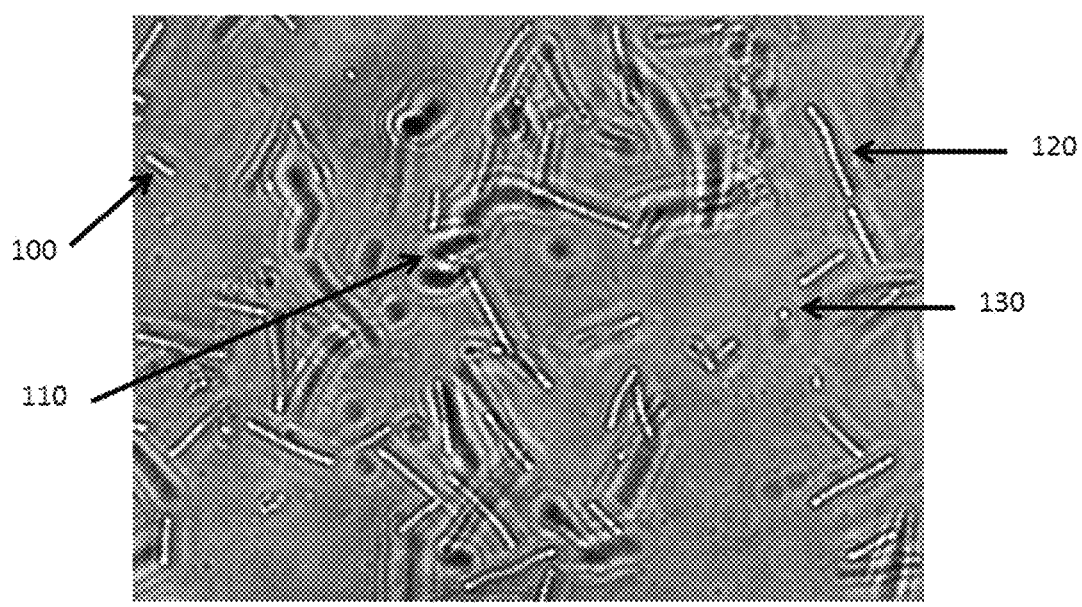
FIG. 1 is a bright field micrograph of a consortium grown on CO2, H2 and O2, which shows the multiple species of microbes, according to various embodiments.

In accordance with the present invention, products, materials, intermediates, and the like such as protein biomass and/or other biological products are produced from the waste gases of industrial processes by cultivating a microbial consortium. Such gases may include $CO_2$, CO, $CH_4$, and $H_2$, thereby reducing environmental pollution while at the same time saving energy and chemical feedstocks. Other trace gases which may be present in the industrial effluent, such as $H_2S$ or $SO_2$, can provide additional nourishment to the autotrophic primary producer bacteria, and removal of such gases provides the added benefit of remediating these toxic GHGs from the gas stream.

In accordance with an exemplary process of the present invention, the desired components of the gas mixtures are introduced into a bioreactor containing one or more cultured strains of microbes that utilize the waste gas components to produce a desired compound. The desired product (biomass, nutraceutical, protein, etc.) is recovered from the aqueous phase in a separate vessel or vessels, utilizing a suitable recovery process for the compound produced. Examples of recovery processes include extraction, distillation or combinations thereof, or other efficient recovery processes. The bacteria are removed from the aqueous phase and recycled to avoid toxicity and maintain high cell concentrations, thus maximizing reaction rates. Cell separation, if desired, is accomplished by centrifugation, membranous ultrafiltration, or other techniques.

The principal object of the present invention is the provision of a process and/or a consortium of microorganisms for the production of products, intermediates, materials, and the like such as biomass, feed ingredients, proteins, vitamins, probiotics, natural antibiotics, organic acids, and the like from carbon dioxide, hydrogen, and oxygen.

Another object of the present invention is the provision of methods, microorganisms and apparatus for the production of items such as biomass, feed ingredients, proteins, vitamins, probiotics, natural antibiotics, and organic acids from the waste gas streams of industrial processes, such as brewing, bioethanol production, cement manufacturing, oil refining, and similar processes that generate waste $CO_2$ and/or $H_2$.

Yet another object of the present invention is the provision of a method, microorganism and apparatus involving continuous gaseous substrate fermentation under aerobic conditions to accomplish the conversion of waste gas streams of certain industrial processes into useful products such as biomass, feed ingredients, proteins, vitamins, probiotics, natural antibiotics, and organic acids.

Other objects and further scope of the applicability of the present invention will become apparent from the detailed description to follow, taken in conjunction with the accompanying drawings wherein like parts are designated by like reference numerals.

DETAILED DESCRIPTION

Microbial strains. *C. necator* has the advantage that it can grow very rapidly and to high density on a mixture of $H_2$, $CO_2$, $O_2$, and it can be continuously cultured for long periods of time without contamination. The same is true for *C. basilensis*, and for *Methyloccocus capsulatus* where CH4 is added or used in place of H2. Bacterial strains for the consortium are selected for being both naturally-occurring (i.e., non-GMO), generally recognized as safe ('GRAS') organisms, or because of their apparent beneficial qualities and apparent lack of negative characteristics, so that they will be broadly suitable for feed and food processing, although GMO organisms designed for a specific purpose (e.g., metabolite production via an engineered pathway) can also be included, if desired. All strains for the invention described herein were obtained as pure, axenic type-cultures from culture collections.

Gas supply. The $CO_2$, $H_2$ and $O_2$ can be supplied from either flue gas collected from an industrial emitter (designated as 'flue gas') or from pure stocks of compressed gas obtained from a gas supplier (designated as 'lab gas'), from process gas produced by an industrial process, from gasifier or pyrolysis output gas, syngas, from the manufacture of cement, from a combustion process, or from any industrial, natural or other process which produces one or more of the desired gases. For production of feed, food, nutraceuticals, biologicals, and the like, an industrial source of waste $CO_2$ that is free of toxic elemental contaminants (e.g., mercury) is preferred. Examples of such sources include $CO_2$ from breweries and bioethanol plants. Hydrogen can be supplied as part of the gas composition of pyrolysis gas, syngas, as an industrial side product from activities such as propylene manufacture, as a component of a mixed gas stream from an oil refinery, or in gas created by steam methane reformation (SMR) process, from compressed gas, or from electrolysis of water. Oxygen can be obtained from atmospheric gas, as a product of electrolysis, or as a component of industrial by-product gas such as cement flue-gas. Embodiments of the invention include methods for collecting and compressing flue gas at an industrial site into transportable pressurized cylinders so that substantial quantities of flue gas can be carried back to the laboratory for analysis and fermentation of the microorganisms. In the laboratory, the $CO_2$ and $O_2$ (derived from either lab gas or flue gas) are further diluted approximately 5-fold with $H_2$ to supply the bacteria with a feedstock mixture that is optimized for growth. For a commercial-scale operation, the fermentation plant can be located near the gas production site, or the gas can be transported by vehicle or pipeline to the biomass production site.

For injection into the fermenter, the gas supply was filtered through 0.2 um filters to remove particles and microorganisms. For small-scale experiments, compressed $H_2$, $CO_2$ and $O_2$ were each regulated to 20 psi. The gases were delivered to a flow proportioner, which sets the relative fraction of the gases, and a variable area flow meter to control the mixture and flow rate into the fermenter. Gas flow was adjusted to between 0.2-1.2 VVM to supply adequate nutrients at each stage of the fermentation. The agitation rate was adjusted between 150-300 rpm to provide thorough mixing.

Nutrient monitoring. The composition of the input and output gas can be measured and monitored to determine the gas uptake rates, the mass balances and the mass transfer efficiency for dissolution of the gas into the solution and the biomass. Key nutrients (such as $NH_4$, $PO_4$ & $SO_4$), can also be monitored and replenished to prevent nutrient limitations that might restrict bacterial growth.

Microbial inocula. The inocula for fermenter runs can be prepared in many ways; each microbial strain may be grown separately, or two or more may be grouped together in a single fermentation. Heterotrophic species are always grown up from pure cultures on heterotrophic medium that is suitable for propagating the particular species (or group of species) being grown. Chemoautotrophic species can be grown on gases, or, in some cases, on heterotrophic media. Photoautotrophic species may be grown using light or heterotrophic media. Some photoautotrophic species are also chemoautotrophic, and thus may be grown on gaseous substrates. Inoculating the bioreactor involves sterile addition of a culture containing one or more of the species into the bioreactor.

In some embodiments, all of the cultures for the consortium are added to the bioreactor, in a short period of time, at the beginning of the fermentation procedure or run.

In some embodiments, chemoautotrophic microbes are added to the bioreactor at the beginning of the fermentation, and the inoculum cultures containing other species are added at later points.

In some embodiments, the timing of the addition, amount and density of culture additions, and method of preparing inocula can be altered to affect the qualities, composition, and/or value of the final product.

In some embodiments, additional inoculations of one or more strains used in the consortia can be added at later times.

In embodiments of the invention, cultures were prepared by growing *C. necator* and the other chemoautotrophic species on H2/CO2/O2 to an $OD_{620}$ ~1 in small bottles of media equipped with gas fittings. Non-chemoautotrophic species were grown in liquid yeast-tryptone medium (YT medium), a well-known and commercially available medium. The bioreactor was inoculated to OD ~0.1. A ca. 5% inoculum is ideal. The pH is controlled with 2N $NH_4OH$. The fermentation is run for up to several days, resulting in $OD_{620}$ of 1-100 or greater. The recovered biomass was analyzed for protein and lipid content and the composition of each product. Proprietary strains, of some embodiments of the invention, of *C. necator* and/or *R. capsulatus*, or other proprietary strains of microbe, were sometimes used in addition to type strains. Embodiments of the invention include several strains of chemoautotrophic species that are adapted to flue gas and therefore tolerant to various toxic gas components, which can be included in the mix if complex industrial flue gas is used as the feedstock. In some cases, additional inoculations with one or more consortia strains were carried out a later time points.

Microbe species commonly used in various embodiments for enablement include those shown in Table 1: The micrograph in FIG. 1 is from a fermentation of all of these except B-3226.

TABLE 1

| Strain | Species | Source |
| --- | --- | --- |
| B-3226 | *Rhodospirillum rubrum*, | (ARS NRRL Type Strain) |
| B-1727 | *Rhodobacter sphaeroides*, | (ARS NRRL Type Strain) |
| B-4276 | *Rhodopseudomonas palustris*, | (ARS NRRL Type Strain) |
| B-14308 | *Bacillus megaterium*, | (ARS NRRL Type Strain) |
| B-356 | *Bacillus subtilis*, | (ARS NRRL Type Strain) |
| B-354 | *Bacillus subtilis*, | (ARS NRRL Type Strain) |
| B-14200 | *Bacillus subtilis* subspecies *subtilis*, | (ARS NRRL Type Strain) |
| B-41406 | *Bifidobacterium animalis* subspecies *animalis*, | (ARS NRRL Type Strain) |
| B-4495 | *Lactobacillus acidophilus*, | (ARS NRRL Type Strain) |
| B-1922 | *Lactobacillus casei* subspecies *casei*, | (ARS NRRL Type Strain) |
| B-4383 | *Cupriavidus necator*, | (ARS NRRL Type Strain) |
| B-14690 | *Cupriavidus necator*, | (ARS NRRL Type Strain) |
|  | *Cupriavidus necator* strain H16 | (ATCC Type Strain) |
|  | *Rhodobacter capsulatus* strain SB-1003 | (ATCC Type Strain) |
| OB213 | *Rhodobacter capsulatus*, | Oakbio, Inc. Proprietary Strain |
| OB311 | *Cupriavidus necator*, | Oakbio, Inc. Proprietary Strain |

Figure 2:
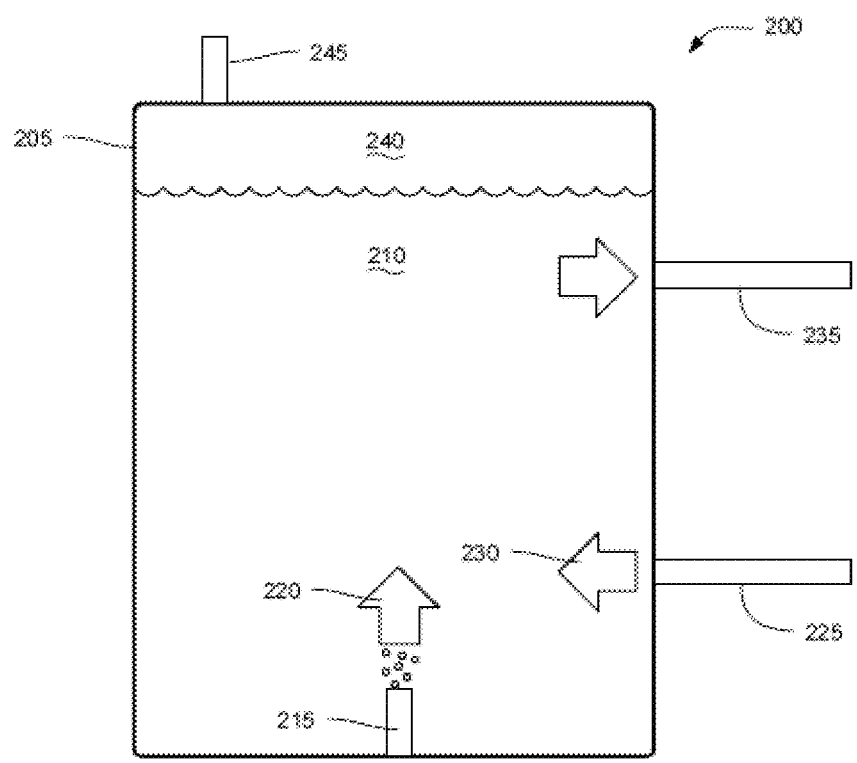
FIG. 2 is a schematic representation of a bioreactor according to an exemplary embodiment of the present invention, according to various embodiments.

Bioreactor Fermentation. A bioreactor for chemoautotrophic synthesis is used for enablement of this invention. Many types and designs of bioreactor are suitable. The critical parts of a bioreactor for cultivation of the product discussed in this application are that there be a vessel which is at least partially filled with liquid medium, in which the microbes are dispersed. The liquid comprises chemicals required for growth of the microbes, examples of which are described below. At least one port exists for introducing the gaseous substrates into the liquid in the bioreactor. The vessel may have a headspace into which gases collect after traversing the fluid in the vessel. An exhaust port allows gases to exit the vessel. Additional ports are present as needed for sensors, addition of liquids or chemicals and removal of product, liquids, or samples for testing, as would be expected to be found on common bioreactors, which are well known in the field of fermentation, cell culture and microbe cultivation. A minimal design bioreactor is shown in FIG. 2. In various embodiments, the invention has been enabled in custom-built 250 ml, 1 L, and 4 L glass flask based bioreactors and in a commercially manufactured New Brunswick Scientific Bio Flo 4500 with the 4-gas handling option. Additional bioreactor designs that can be used in conjunction with the present invention can be found in U.S. patent application Ser. No. 13/204,649 filed on Aug. 6, 2011 and entitled "Chemoautotrophic Bioreactor Systems and Methods of Use" which is incorporated herein by reference. Bioreactors for embodiment of this invention can comprise one or more vessels and/or towers or piping arrangements, and can comprise, for example, a Continuous Stirred Tank Reactor (CSTR), an Immobilized Cell Reactor (ICR), a Trickle Bed Reactor (TBR), a Bubble Column, a Gas Lift Fermenter, a Static Mixer, a Fluidized Bed, an Up-flow or Down-flow, a continuous, batch or loop reactor, or any other vessel or device suitable for maintaining suitable gas-liquid contact. In some embodiments, the bioreactor may comprise a first growth vessel and a second chemoautotrophic synthesis vessel, while in other embodiments a single vessel is used throughout both of the growth and synthesis stages.

In some embodiments, a gas recirculation system can be used to improve the conversion efficiency, particularly during a continuous process, in order to reduce the total gas requirement. Continuous harvesting of the cell mass is advantageous for a commercial production process, and can be implemented through the continuous removal of cell broth and the continuous replenishing of medium, in order to maintain the culture volume and cell density. Fermentations were run at a constant or varied temperatures between 15 and 70 C, but the preferred temperature is 30 C.

Monitoring cell growth and species diversity. To monitor the progress of cell growth and verify the species diversity of the culture, samples can be periodically removed for analysis, or the bioreactor system can comprise analytic equipment. In enabling the technology in some embodiments, characterization included microscopy of cell morphology, an example of which is shown in FIG. 1 (from the completion of a run), which shows that the species diversity was maintained. Wet mounts of the culture were observed using brightfield microscopy with an Olympus BX research microscope equipped with an Amscope CCD camera. Micrographs were generated using the Amscope software for imaging and data storage. Species diversity can also be monitored and quantitated using methods well known in the art, such as analysis of 16S rRNA genes, 23S rRNA genes, or other genetic markers and phenotypic indicators (Jovel et al., 2016). Growth behavior was characterized by optical density (OD) measurements at 620 nm using an ICN Titer-Tek 96-well plate reader. Aliquots of each fermenter sample (200 ul) were measured in duplicate to plot the growth curves.

Carbon capture. Carbon capture from a new source of flue gas can be verified by performing headspace gas analysis, as well as growth experiments that use the flue gas as the sole carbon source for bacterial biomass production. The dry weight of each culture can also be determined by centrifuging the culture, washing the pellet, drying the cells in a lyophilizer, and weighing the lyophilized cells.

Gas mixing. For hydrogen fermentations typically, the CO2 feedstock or raw flue gas was diluted with pure hydrogen with ratios of about 8:1 to 1:1 (H2:CO2, v/v), resulting in a final CO2 concentration of about 50%-1% or less. The O2 concentration is ideally 3-12%. For methane fermentations, typically the methane concentration is between 80% to 5%, CO2 is between 40%-1%, and oxygen is 50% to 5%. In either system, CO can be up to 10%, and a variety of other gases may be present, including sulfur oxides, nitrogen oxides, hydrogen sulfide, molecular nitrogen or other gases found in the gas source.

Culture medium. Many different mineral media recipes can be used, and varying the media is one of the ways the characteristics of the final product can be influenced. In various embodiments, typically a mineral salts medium (modified from Repaske & Mayer, 1976) was used that contained no organic carbon or complex nutrients: Na2HPO4.2H2O 4.5 g/L, KH2PO4 1.5 g/L, NH4Cl 1.8 g/L, MgSO4.7H2O 0.11 g/L, NaHCO3 0.2 g/L, FeSO4.7H2O 12 mg/L, CaCl2.2H2O 10 mg/L, ZnSO4.7H2O 100 µg/L, MnCl2.4H2O 30 µg/L, H3BO3 300 µg/L, CoCl2.6H2O 200 µg/L, CuCl2.2H2O 10 µg/L, NiCl2.6H2O 20 µg/L, Na2MoO4.2H2O 30 µg/L.

Concentration and harvesting. Biomass product can be harvested through many methods, such as filtration, gravity separation, or other method, of which many are industrially practiced. Drying can be by spray drying, freeze drying, thermal drying, desiccation or many other methods, many of which are currently practiced industrially.

Brief heat treatment is useful if the cells must be made non-viable prior to further processing. Due to the fact that lyophilization is more energy-intensive, it is more suitable for processing very high-value products that require gentle processing. The dried material can be easily blended with other ingredients to form a nutritious fish feed that can replace aquafeed products that typically rely on fishmeal for protein, fatty acids, and other nutrients. The amino acid composition of the dried material from a 30 L batch of cultivated consortium (Table 2) compares favorably to that of fishmeal (IAFMM Report, 1970)

In the below referenced demonstration, cell suspensions were removed from the fermenter via the sterile exit port. The supernatant can then be removed by centrifugation in a standard or process centrifuge at ca. 4,000×g or greater to form a cell pellet. The cells are then washed in a low-salt buffer solution, and then re-pelleted. The final cell paste was then freeze dried to a powder using a commercial MTS lyophilizer.

TABLE 2

An example of the amino acid composition of a consortium. A sample of the consortia grown, in various embodiments, consisting of chemoautotrophs, photoautotrophs, and probiotic heterotrophs, cultivated at the 30 L scale in a New Brunswick Scientific BioFlo 4500 Bioreactor with 4-gas input and control option. Amino acid composition analysis was conducted by NP Analytical Laboratories (St. Louis, MO).

| Amino Acid | g/100 g Dried Biomass |
|---|---|
| Aspartic Acid | 4.49 |
| Threonine | 2.40 |
| Serine | 1.79 |
| Glutamic Acid | 7.31 |
| Proline | 1.67 |
| Glycine | 2.15 |
| Alanine | 3.24 |
| Valine | 3.34 |
| Methionine | 1.16 |
| Isoleucine | 2.60 |
| Leucine | 3.24 |
| Tyrosine | 1.71 |
| Phenylalanine | 1.99 |
| Histidine | 0.930 |
| Lysine | 3.48 |
| Arginine | 2.45 |
| Cysteine | 0.312 |
| Tryptophan | 0.519 |

PATENT CITATIONS

| Cited Patent | Filing Date | Publication Date | Applicant | Title |
|---|---|---|---|---|
| U.S. Pat. No. 9,267,158 B2 | Jan. 7, 2016 | Jul. 26, 2016 | Intrexon Corp. | Biological production of multi-carbon compounds from methane. |
| U.S. Pat. No. 7,579,163 B2 | Aug. 16, 2002 | Aug. 25, 2009 | Statoil Asa | Method of fermentation |
| U.S. Pat. No. 6,340,581 B1 | Dec. 23, 1998 | Jan. 22, 2002 | Bioengineering Resources, Inc. | Biological production of products from waste gases |
| U.S. Pat. No. 9,206,451 B2 | Sep. 11, 2012 | Dec. 8, 2015 | Oakbio, Inc. | Chemoautotrophic conversion of carbon oxides in industrial waste to biomass and chemical products |
| EP 1419234 A1 | Aug. 16, 2002 | May. 19, 2004 | Cockbain, Julian, Norferm DA | Method of fermentation |

FIG. 1 shows a bright field micrograph of a consortium grown on CO2, H2 and O2, taken May 15, 2017. This picture shows a mix of chemoautotrophic and heterotrophic microbes grown with CO2 as a primary carbon source and H2 as a primary energy source. A short, thin rod 100, a medium-length, fat rod 110 (characteristic of *C. necator*), a long rod 120 (characteristic of *B. megaterium*), and a coccus 130 are indicated by arrows.

FIG. 2 shows a schematic representation of a bioreactor 200 as one example of a bioreactor that is suitable for culturing a consortium on gas. Bioreactor 200 can comprise either a synthesis vessel for use in conjunction with a separate growth vessel, or can comprise a vessel suitable for both of the growth and synthesis stages. In FIG. 2, bioreactor 200 includes a vessel 205 that in operation holds a quantity of a liquid medium 210 containing the chemoautotrophic micro-organisms and other microbes in culture. The bioreactor 200 also includes a substrate port 215 through which a gaseous substrate 220 can be introduced into the vessel 205 for introduction into the liquid medium 210, a media inlet port 225 through which fresh media 230 can be introduced into the vessel 205 for introduction into the liquid medium 210, and a media outlet port 235 through which the medium 210 can be removed, for example, to harvest biomass and/or chemical products. The bioreactor 200 can also comprise a headspace 240 and a gas release valve 245 to vent gases from the headspace 240. In some embodiments, the media outlet port 235 and the media inlet port 225 are connected via a system which harvests biomass 170 and reconditions the medium 210 for recirculation. In some embodiments, the gas release valve 245 is attached to a system which recirculates the gaseous substrate back to the substrate port 215, and may make additions or subtractions to optimize the gas composition.

Deposit of Biological Material

The following microbes have been deposited with the American Type Culture Collection, 10801 University Boulevard, Manassas, Va. 20110-2209, USA (ATCC):

TABLE 3

| Microbe Designation | ATCC No. | Deposit Date |
|---|---|---|
| *Rhodobacter capsulatus* OB-213 | PTA-12049 | Aug. 25, 2011 |

This deposit was made under the provisions of the Budapest Treaty on the International Recognition of the Deposit of Microorganisms for the Purpose of Patent Procedure and the Regulations thereunder (Budapest Treaty). This assures maintenance of viable cultures for 30 years from the date of the deposit. The organisms will be made available by ATCC under the terms of the Budapest Treaty, and subject to an agreement between Oakbio, Inc. and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.12 with particular reference to 886 OG 638).

The assignee of the present application has agreed that if the cultures on deposit should die or be lost or destroyed when cultivated under suitable conditions, they will be promptly replaced on notification with a viable specimen of the same culture. Availability of the deposited strain is not to be construed as a license to practice the invention in contravention of the rights granted under the authority of any government in accordance with its patent laws.

What is claimed is:

1. A method comprising:

providing a consortium of chemoautotrophic and photoautotrophic bacteria and heterotrophic microbes within a system, the system including a fermentation vessel filled with an aqueous medium comprising the consortium, the fermentation vessel having an input port into which gaseous substrates are introduced into the aqueous medium, the fermentation vessel further having an exhaust port through which gases exit the fermentation vessel, wherein the aqueous medium comprises inorganic anions and inorganic cations, and wherein the aqueous medium contains a concentration of no more than 0.05% of each of added sugars, yeast extract, tryptone, and organic carbon compounds, the consortium including chemoautotrophic bacteria from the genera *Cupriavidus, Rhodococcus*, or *Methylococcus*, photoautotrophic bacteria from the genera *Rhodobacter, Rhodospirillum, Rhodopseudomonas*, or *Arthrospira*, and heterotrophic microbes from the genera of *Bacillus, Bacteroides, Bifidobacterium, Lactobacillus, Lactococcus, Leuconostoc, Acidilactici, Pediococcus, Propionibacterium*, or *Streptococcus*;

introducing a first gaseous substrate into the input port, the first gaseous substrate including carbon dioxide;

introducing a second gaseous substrate into the aqueous medium, the second gaseous substrate including predominantly hydrogen gas ($H_2$), wherein either of the first or second substrates additionally includes oxygen gas ($O_2$), wherein a volume ratio of $H_2$ in the second gaseous substrate to $CO_2$ in the first gaseous substrate is in the range of 1:1 to 8:1; and harvesting cells of the bacteria from the system to generate a biomass product that has enhanced nutritional value compared to the biomass that the same chemoautotrophic bacteria would produce if grown alone.

* * * * *